United States Patent [19]

Raaf et al.

[11] 4,397,837

[45] Aug. 9, 1983

[54] PROCESS AND COMPOSITION FOR THE REMINERALIZATION AND PREVENTION OF DEMINERALIZATION OF ANIMAL TEETH INCLUDING HUMANS

[75] Inventors: Helmut Raaf, Karlsruhe-Waldstadt; Helmut Harth, Mainz; Helmar R. Wagner, Darmstadt-Arheilgen, all of Fed. Rep. of Germany

[73] Assignee: Blendax-Werke R. Schneider GmbH & Co., Mainz, Fed. Rep. of Germany

[21] Appl. No.: 540,862

[22] Filed: Jan. 14, 1975

Related U.S. Application Data

[63] Continuation of Ser. No. 327,466, Jan. 29, 1973, abandoned.

[30] Foreign Application Priority Data

Feb. 2, 1972 [GB] United Kingdom ............... 4848/72

[51] Int. Cl.³ .................... A61K 7/16; A61K 7/18; A61K 23/42; A61K 33/16
[52] U.S. Cl. .................................. 424/51; 424/52; 424/57; 424/128; 424/151; 424/154
[58] Field of Search .................. 424/48, 51, 52, 57, 424/128, 151, 154

[56] References Cited

U.S. PATENT DOCUMENTS 3,175,951 3/1965 Tucker et al. .................. 424/52
3,679,360 1/1972 Rubin et al. .................. 424/128 X

FOREIGN PATENT DOCUMENTS 1090340 11/1967 United Kingdom .

OTHER PUBLICATIONS

Souder et al., J. Am. Dental. Assoc., 31, No. 23, (12/1/44), pp. 1579–1586.
Public Health Reports, 63, No. 38, 9/17/48, pp. 1215–1221.
Feagin et al., Arch. Oral Biology, vol. 16, pp. 535–548, (1971).

Primary Examiner—Douglas W. Robinson
Attorney, Agent, or Firm—Connolly and Hutz

[57] ABSTRACT

Compositions for the remineralization and prevention of demineralization of the teeth of animals including humans in the form of two phases, one phase containing a water-soluble calcium compound and the other phase containing a water-soluble phosphate and optionally a water-soluble fluorine compound. The concentration of calcium and phosphate ($PO_4$) ions is about 50 to 35,000 ppm and 50 to 40,000 ppm respectively, and the amount of fluorine compound is about 0.01 to 5.0%, all by weight of the total composition. The compositions may also contain at least one of a conventional flavoring substance, aroma substance, surfactant, astringent, polishing agent, thickener and preservative.

10 Claims, No Drawings

PROCESS AND COMPOSITION FOR THE REMINERALIZATION AND PREVENTION OF DEMINERALIZATION OF ANIMAL TEETH INCLUDING HUMANS

This application is a continuation of application Ser. No. 327,466 filed Jan. 29, 1973 and now abandoned.

This invention concerns a process for the remineralization and the prevention of demineralization of animal, including human, teeth and to a composition for carrying out this process.

J. A. Head in 1910, in Dent. Cosmos 52, 46 described for the first time in detail the softening and re-hardening of human dental enamel. Since that time, numerous investigations have been carried out on the demineralization and remineralization of dental enamel within the general framework of research into caries.

By demineralization of the dental enamel is understood the loosening of the structure of the enamel and the formation of voids between the crystals. Such demineralization occurs in the initial phase of enamel caries, before a cavity is detectable. It leads to a reduction of the crystal size; the crystals are degraded, starting from the surface. As the carious process progresses, severe destruction of the crystals occurs.

In carious demineralization, the apatite crystals are degraded. A comprehensive survey of the state of the researches and of the problem of mineralization, demineralization and remineralization of dental enamel is to be found in H. Lenz, Deutsche Zahnärztliche Zeitschrift, Volume 24 (1969), pages 460-472.

Attempts have recently been made to arrest or to prevent the progress of caries by artificial remineralization of the dental enamel, that is to say by the incorporation of calcium ions and phosphate ions, and also to reverse the demineralization which has occurred in the dental enamel, again by supplying calcium ions and phosphate ions.

Thus it has already been proposed to supply calcium ions and phosphate ions to human dental enamel by adding various compounds containing calcium and phosphate to food. In this context, attention need only be drawn to the basic investigation by F. J. McClure in Journal of Dental Research, Vol. 42 (1963), 693-99, where it is established that dental caries in rats is reduced by adding various inorganic and organic phosphates to the diet.

It has also already been proposed to add compounds containing calcium ions and phosphate ions to dental cosmetics which are used topically, and thus to achieve a remineralization of the dental enamel. In this way, however, no more satisfactory results, that is to say adequate remineralization of the dental enamel by the incorporation of calcium ions and phosphate ions, were achievable than in the case of using water-insoluble calcium phosphates, for example dicalcium phosphate, which has also already been described (British Patent Specification No. 1,102,024), for example in chewing gum. This is presumably due to the fact that as a result of the low solubility in water of these calcium phosphates and of the consequent inadequate dissociation, calcium ions and phosphate ions are not available in sufficient amount to effect satisfactory incorporation of these ions into the demineralized dental enamel.

British Patent Specification No. 1,090,340 describes a process for the re-hardening of dental enamel which is characterized in that a supersaturated solution of an apatite material, which is stabilized with an isotonic sodium chloride solution, is produced in the presence of teeth by reaction of a mixture of a water-soluble calcium salt, a water-soluble phosphate salt and a water-soluble fluoride salt. This material is intended to be incorporated into the demineralized dental enamel. In this process, no real absorption of calcium ions, phosphate ions and fluoride ions by the dental enamel occurs, and hence no remineralization of the softened dental enamel, a deposit of fluorohydroxyapatite being merely produced on the surface of the dental enamel. In addition, the requisite presence of sodium chloride presents considerable problems in the manufacture of a dental cosmetic, which, as is known, not only needs to meet therapeutic, that is to say caries-prophylactic, requirements but also requirements as to flavour, since a salty flavour can only be masked with difficulty and renders such products unattractive to the consumer.

It is the object of the present invention to provide a process and especially a composition for the remineralization and the prevention of demineralization of animal, including human, teeth, which process and composition are capable of effectively incorporating calcium ions, phosphate ions and, if desired, fluoride ions into the dental enamel, the composition also being easily usable by the consumer and not differing significantly, in flavor and appearance, from customary dental cosmetics.

This problem is solved by applying to the teeth a composition which is present in two phases which do not react with one another, one phase containing at least one water-soluble calcium compound, together with customary vehicles, and the other phase containing at least one water-soluble organic and/or inorganic phosphate and optionally a water-soluble fluorine compound. In this way the ions which effect remineralization can be absorbed successively by the dental enamel and their reaction causes re-hardening of demineralized areas in the dental enamel.

The compositions of the invention give substantially improved remineralization and prevention of demineralization of human teeth as compared with prior art compositions.

The compositions of the invention can be used in conventional forms, for example in solution, paste or gel form or as a solid substance; the only requirement is that until use the phase containing calcium remains separate from the phase containing phosphate. Thus, for example, when the preparation is in a paste form, the teeth can first be cleaned with a phase containing the water-soluble calcium compound and can subsequently be cleaned again with the phase containing the water-soluble phosphate. A particularly elegant solution is to accommodate the two phases which are to be kept separate in two-compartment tubes or two-compartment aerosol cans, the two phases being kept separate during storage and also being dispensed separately from one another. A suitable tube is described, for example, U.S. Pat. No. 3,747,804.

A further elegant solution is to introduce the two phases into a two-layer mouthwash, a multi-layer chewing gum, into multilayer dragees or into two-layer bonbons; it is also possible to employ an emulsion or dispersion where the calcium compound and the phosphate are present in different phases. It is also possible to provide the water-soluble phosphate or the water-soluble calcium compound with a coating (that is to say to encapsulate it), this coating being such as only to release the active substance, through the action of heat or through mechanical action, when the product is used. It is also possible to use the materials by first brushing a relatively highly concentrated solution or a gel of one compound onto the teeth and thereafter applying the second active substance. Such a treatment, which can be carried out by the dentist or the individual, only needs to be repeated occasionally when the concentration of active substance is suitable.

It has been found in animal experiments that these two-phase preparations give a substantially improved caries-protective activity as compared to the preparations hitherto proposed for remineralization, which are in one phase.

As calcium compound it is in principle possible to employ, in the preparations of the invention, all water-soluble toxicologically harmless calcium compounds. A compound is considered to be water-soluble when at least 0.25 gram thereof dissolves in 100 ml of $H_2O$ at 20° C.

Suitable water-soluble calcium compounds are, for example, calcium chloride, calcium nitrate, calcium acetate, calcium gluconate, calcium benzoate, calcium citrate, calcium formate, calcium fumarate, calcium lactate, calcium butyrate and calcium isobutyrate, calcium malate, calcium maleate, calcium propionate, calcium valerate or mixtures of water-soluble calcium compounds. In the compositions of the invention for the remineralization of human dental enamel, at least about 50 ppm of calcium ions should be present; the upper limit is about 35,000 ppm of calcium ions.

Suitable water-soluble inorganic phosphates within the scope of the present invention are, for example, the alkali salts and ammonium salts of orthophosphoric acid, such as potassium, sodium or ammonium orthophosphate, water-soluble alkali metaphosphates or alkali polyphosphates or mixtures of these substances.

Particular water-soluble organic phosphates are sugar esters of orthophosphoric acid and esters of phosphoric acid and polyhydric alcohols. As examples there may be mentioned fructose phosphate, sorbitol phosphate, glucose phosphate, sucrose phosphate, glycerophosphate, mannitol phosphate and inositol phosphate and their water-soluble salts. The concentration of the $PO_4$ ions is preferably about 50 to 40,000 ppm; solubility in water is defined as in the case of the calcium compounds.

Preferably, the compositions of the invention for the remineralization or prevention of demineralization of human teeth also contain water-soluble fluorine compounds, the caries-prophylactic activity of which has for a long time been considered to be established. These compounds are preferably present in the phase containing phosphate in order to avoid the formation of sparingly soluble calcium floride.

Suitable fluorine compounds of which the preferred concentration range is about 0.01 to 5.0% by weight of the total composition, are the alkali fluorides such as sodium, potassium, lithium or ammonium fluoride, tin fluoride, indium fluoride, zirconium fluoride, copper fluoride, nickel fluoride, palladium fluoride, fluorozirconates such as sodium, potassium or ammonium fluorozirconate or tin fluorozirconate, fluorosilicates, fluoroborates, fluorostannites or fluoro phosphates, especially sodium, potassium, lithium or ammonium monofluorophosphate or aluminum fluorophosphate. Organic fluorides, such as the known amine fluorides are also suitable for use in the compositions of the invention.

The compositions of the invention can contain conventional additives for dental and oral cosmetics. As such there may in particular be mentioned flavouring substances and aroma substances such as, for example, menthol and its esters, for example 1-menthyl-ethyl-carbonate, peppermint oil or eucalyptus oil, surfactants, astringents and preservatives.

When one or both phases of a dental cosmetic of the invention are in the form of a paste, such pastes usually contain conventional substances of polishing action.

It is, of course, also possible to manufacture one or both phases in the form of a transparent gel, the gel-forming agents to be used including known thickeners, for example the alkali salts of polyacrylic acid, and also preferentially dehydrated silicon dioxide gels of particle size about 2 to 20 microns and specific surface area about 200 to 900 $m^2/g$.

The following Examples illustrate the invention: In the Examples and elsewhere herein parts and percent are by weight unless otherwise stated.

EXAMPLE 1

In a two-compartment tube, one compartment was filled with a toothpaste of composition A and the other with a toothpaste of composition B. The two pastes are completely separated from one another in the tube. The compositions of the pastes, in % by weight, are as follows:

|  | Toothpaste | |
|---|---|---|
|  | A | B |
| Calcium chloride.2 $H_2O$ | 1.80 | — |
| Disodium hydrogen phosphate | — | 1.00 |
| Phytic acid | — | 0.35 |
| Sodium fluoride | — | 0.22 |
| Carboxymethylcellulose | 1.40 | 1.40 |
| Benzoic acid | 0.10 | 0.10 |
| Sodium saccharine | 0.10 | 0.10 |
| Aroma substances | 1.50 | 1.50 |
| Polyglycol 600 | 2.50 | 2.50 |
| Sorbitol, 70% strength | 10.00 | 10.00 |
| Glycerol | 10.00 | 10.00 |
| Polymethyl methacrylate powder | 38.00 | 38.00 |
| Water | 34.60 | 34.83 |

EXAMPLE 2

Two pastes A and B were prepared, of which paste A consists of a customary paste base and contains a calcium compound. In contrast, paste B, which contains water-soluble phosphates, is in the form of a transparent gel.

The teeth are first cleaned with paste A and subsequently with paste B.

| Toothpaste A: | | |
|---|---|---|
| Calcium gluconate | 5.60 | % by weight |
| Carboxymethylcellulose | 1.70 | " |
| Methyl p-hydroxybenzoate | 0.12 | " |
| n-Propyl p-hydroxybenzoate | 0.03 | " |
| Sodium saccharine | 0.05 | " |
| Aroma substances | 1.50 | " |
| Sodium lauryl-sulphoacetate | 1.70 | " |
| Liquid Paraffin | 1.50 | " |
| Sorbitol 70% strength | 20.00 | " |
| Polymethylmethacrylate powder | 35.00 | " |
| Water | 32.80 | " |
| Toothpaste B, in the form of a gel: | | |
| Sodium glycerophosphate | 0.85 | " |
| Potassium dihydrogen phosphate | 0.50 | " |
| Disodium hydrogen phosphate | 0.70 | " |

| | | |
|---|---|---|
| Sodium fluoride | 0.22 | " |
| Caragheenate | 0.30 | " |
| Ethyl p-hydroxybenzoate | 0.15 | " |
| Sodium saccharine | 0.05 | " |
| Aroma substances | 1.10 | " |
| Dyestuff (L-Red 3, Amaranth) | 0.01 | " |
| Sodium lauryl-sulphate | 2.00 | " |
| Glycerol | 60.00 | " |
| Precipitated silica | 21.00 | " |
| Water | 13.12 | " |

EXAMPLE 3

Two mouthwashes for successive rinsing of the mouth were prepared, having the following composition (data in % by weight):

| Mouthwash A | | Mouthwash B | |
|---|---|---|---|
| Calcium chloride, anhydrous | 1.10 | $KH_2PO_4$ | 0.70 |
| Sodium saccharine | 0.01 | $Na_2HPO_4.2\ H_2O$ | 0.90 |
| Aroma substances | 0.05 | Sodium saccharine | 0.01 |
| Emulsifier | 0.10 | Aroma substances | 0.05 |
| Glycerol | 5.00 | Emulsifier | 0.10 |
| Ethanol, concentrated | 7.00 | Glycerol | 5.00 |
| Water | 86.74 | Ethanol, concentrated | 7.00 |
| | | Water | 86.24 |

EXAMPLE 4

A two-layer (I and II) chewing gum was produced as follows (data in % by weight):

1.60 of spearment oil/menthol, 0.50 of glycerol, 16.80 of glucose, (I) 54.50 and (II) 54.33 of sorbitol, (I) 1.82 of $Ca\ Cl_2.2H_2O$ and (II) a mixture of 0.65 of $Na_2HPO_4.2H_2O$, 0.55 of $KH_2PO_4$ and 0.82 of sodium glycerophosphate, were separately mixed into 24.75 portions of a customary gum base and each resulting composition was separately well kneaded and rolled into strips, and the two strips were united under pressure, so that a two-layer ribbon was produced, which was cut into sections and packaged.

EXAMPLE 5

Into two batches of a bonbon base, consisting respectively of
13.00% by weight of gum arabic
13.00 gelatin
21.00 powdered sorbitol
0.05 sodium saccharine
0.01% by weight of food dyestuff
0.50 fruit essence and
(I) 49.94% by weight of or
(II) 51.47% by weight of water,
were incorporated, in (I) 2.50% by weight of calcium gluconate, and in II
0.32% by weight of $Na_2HPO_4$,
0.35% by weight of $KH_2PO_4$ and
0.30% by weight of sodium glycerophosphate
and bonbons were formed separately from each batch in the usual manner, in different colours if desired. Pairs of bonbons of the differing batches were packaged as a "bonbon pair".

It is also possible to manufacture solid preparations, such as chewing gum, bonbons or dragees, with more than two layers, in such a way that alternately a calcium compound or a phosphate compound and, optionally, a fluorine compound, are incorporated into each layer, so that, on chewing or sucking, calcium ions, phosphate ions and, optionally, fluoride ions, are released from the various layers.

What is claimed is:

1. Process for remineralizing demineralized dental enamel of the tooth with a precipitate bound to the tooth structure, said process comprising the steps of applying first ions to the tooth surface so that said first ions diffuse through the tooth surface into demineralized dental enamel and thereafter applying second ions to the tooth surface into demineralized dental enamel and form a precipitate with previously applied first ions in said dental enamel, said first ions comprising one of either calcium ions or phosphate ions, said second ions comprising the other of either calcium ions or phosphate ions, said calcium ions being applied in the form of a solution comprising from about 0.005 to about 3.5% of calcium ion from a water-soluble calcium salt which is compatible in the oral environment, said phosphate ions being applied in the form of a solution comprising from about 0.005 to about 4% of phosphate ions a water-soluble phosphate salt which is compatible in the oral environment, each of the applications being carried out for a time period consistent with normal dental care habits.

2. Process as recited in claim 1, in which said first ions comprise calcium ions.

3. Process as recited in claim 1, in which said second ions comprise phosphate ions and fluoride ions.

4. Process as recited in claim 3, in which said second ions are applied in the form of a solution comprising from about 0.005 to about 4% of a water-soluble phosphate ion and from about 0.01 to about 5% of a water-soluble fluoride ion, said ions being from salts which are compatible in the oral environment.

5. Process as recited in claim 1, in which said calcium salt is calcium chloride and in which said phosphate salt is disodium phosphate.

6. Process as recited in claim 1, comprising applying the first ions in the form of a toothpaste and applying the second ions in the form of a mouthwash.

7. Process as recited in claim 1, comprising applying the first ions in the form of a toothpaste and applying the second ions in the form of a toothpaste.

8. Process as recited in claim 1, comprising applying the first ions in the form of a mouthwash and applying the second ions in the form of a mouthwash.

9. Process as recited in claim 1, comprising applying the first ions in the form of a mouthwash and applying the second ions in the form of a toothpaste.

10. Process as recited in claim 1 in which fluoride ions are applied along with the phosphate ions.

* * * * *